(12) United States Patent
Rogers et al.

(10) Patent No.: US 6,898,990 B2
(45) Date of Patent: May 31, 2005

(54) SAMPLING CARTRIDGE FOR GAS SAMPLING APPARATUS

(75) Inventors: William E. Rogers, Troy, NY (US); Adam C. Bailey, Albany, NY (US); Michael S. Cummings, Saratoga, NY (US); Lauren R. Basch, East Greenbush, NY (US)

(73) Assignee: Rupprecht & Pataschnick Company, Inc., East Greenbush, NY (US)

( * ) Notice: Subject to any disclaimer, the term of this patent is extended or adjusted under 35 U.S.C. 154(b) by 0 days.

(21) Appl. No.: 10/835,721

(22) Filed: Apr. 30, 2004

(65) Prior Publication Data

US 2004/0200297 A1 Oct. 14, 2004

Related U.S. Application Data

(60) Division of application No. 10/419,535, filed on Apr. 21, 2003, now Pat. No. 6,769,316, which is a continuation-in-part of application No. 10/177,749, filed on Jun. 21, 2002.

(51) Int. Cl.⁷ ............................................... G01N 1/00
(52) U.S. Cl. ................................................. 73/864.25
(58) Field of Search ........................ 73/863.25, 863.23, 73/863.24, 863.31, 863.57, 863.81, 863.82, 863.85, 863.83, 864.64, 28.01, 28.04, 863.22, 863.01, 863.52, 863.71

(56) References Cited

U.S. PATENT DOCUMENTS

| 3,295,359 A | 1/1967 | Peck ............................. 73/28 |
| 3,540,261 A | 11/1970 | Scoggins ....................... 73/28 |
| 3,657,920 A | 4/1972 | Teel et al. ....................... 73/28 |
| 4,277,682 A | 7/1981 | Madelaine et al. .......... 250/380 |
| 4,628,749 A * | 12/1986 | Rafter, Jr. .................. 73/863.71 |
| 4,795,612 A | 1/1989 | Keller .......................... 422/64 |
| 4,951,749 A | 8/1990 | Carroll ........................ 166/264 |
| 5,265,483 A * | 11/1993 | Farrell et al. ............. 73/863.86 |
| 5,404,762 A | 4/1995 | Rodgers et al. ................ 73/863 |
| 5,468,968 A | 11/1995 | Bailey et al. ................ 250/435 |
| 5,553,507 A | 9/1996 | Basch et al. ............. 73/863.01 |
| 5,646,357 A | 7/1997 | Ogden et al. ............. 73/863.31 |
| 5,717,147 A | 2/1998 | Basch et al. ............. 73/863.23 |
| 5,898,114 A | 4/1999 | Basch et al. ............. 73/863.23 |

(Continued)

FOREIGN PATENT DOCUMENTS

| DE | 202 15 855 | 2/2003 | ............. B01L/9/00 |
| EP | 0964241 A1 | 12/1999 | |
| WO | WO 98/08072 | 2/1998 | ............. G01N/1/24 |
| WO | WO 02/31468 | 4/2002 | ............. G01N/1/24 |
| WO | WO 02/40964 | 5/2002 | ............. G01N/1/22 |

OTHER PUBLICATIONS

Camel v et al: "*Trace enrichment methods for the determination or organic pollutants in ambient air*" Journal of Chromatography A. Elseview Science, NL, vol. 710, No. 1, Aug. 25, 1995, pp. 3–19.

*Primary Examiner*—Robert Raevis
(74) *Attorney, Agent, or Firm*—Heslin Rothenberg Farley & Mesiti P.C.

(57) ABSTRACT

A sampling cartridge for a gas sampling apparatus includes a shell having a cylindrical wall and a sampling window extending through the wall. A pair of spools are coaxially and internally positioned within the shell. The spools are independently rotatable relative to the shell. A first spool may include multiple interval sample collectors while the second spool includes a duration sample collector. Each spool also has a window closing surface which is positioned adjacent the window whenever an access door of the gas sampling apparatus is opened. The sampling cartridge may also include a fully encapsulated section of sample collector material as a negative control, and an integral RF tag for storing chain of custody information including personal identification information of a cartridge replenisher.

4 Claims, 11 Drawing Sheets

U.S. PATENT DOCUMENTS

| | | |
|---|---|---|
| 5,915,268 A | 6/1999 | Linker et al. ................. 73/23.2 |
| 6,023,982 A | 2/2000 | Basch et al. ............. 73/863.25 |
| 6,138,521 A | 10/2000 | Basch et al. ............. 73/863.25 |
| 6,167,107 A | 12/2000 | Bates .......................... 377/10 |
| 6,192,767 B1 | 2/2001 | Fiorina .................... 73/863.21 |
| 6,321,609 B1 | 11/2001 | Mengel et al. ........... 73/863.21 |
| 6,435,043 B1 | 8/2002 | Ferguson et al. ........ 73/863.22 |
| 2001/0029793 A1 | 10/2001 | Moler et al. ............. 73/863.22 |
| 2002/0083780 A1 | 7/2002 | Duggan et al. ............... 78/863 |

* cited by examiner

SAMPLING CARTRIDGE FOR GAS SAMPLING APPARATUS

CROSS-REFERENCE TO RELATED APPLICATIONS

This application is a division of Ser. No. 10/419,535, filed Apr. 21, 2003 now U.S. Pat. No. 6,769,316, which is a continuation-in-part of commonly assigned U.S. application Ser. No. 10/177,749, filed Jun. 21, 2002, the entire contents of which applications is incorporated herein by reference.

FIELD OF THE INVENTION

This invention relates generally to gas samplers, and more particularly to sampling cartridges for collecting and detecting particulate in a gas.

BACKGROUND OF THE INVENTION

Conventional gas samplers for collecting particulate include a housing having a vacuum pump for drawing gas past a collector such as a filter paper, a glass fiber filter media, a filter cassette or an activated carbon cartridge.

Limitations with such conventional gas samplers for collecting particulate include the vacuum pump generally producing a low flow rate of gas to be sampled, the filter becoming clogged, and the vacuum pump being noisy.

A high-flow rate, low-noise, gas sampling apparatus which overcomes the above limitations and may be used for collecting particulates such as biological, chemical, and radioactive material from a gas on a collector such as an impaction collector is disclosed in commonly assigned U.S. patent application Ser. No. 10/177,749. This sampler includes a housing having an inlet and an outlet, and a fan disposed within the housing for drawing the gas into the inlet, past the collector for sampling, and exhausting the gas through the outlet. The sample collector preferably comprises a foam or porous cloth material of the type described in U.S. Pat. No. 6,435,043, entitled "Impaction Substrate and Methods of Use", the entire contents of which is incorporated by reference herein. The fan is operable to produce a flow of gas through the housing of greater than about 50 liters per minute, and preferably greater than about 200 liters per minute, with a noise level emitted from the apparatus of less than about 60 decibels. The sampler may be configured as a compact, unobtrusive, portable, lightweight apparatus for use in various indoor or outdoor locations. It may also include a sensor for the detection of radioactive material collected on the collector, and a processor for monitoring the sampling, and may be linked to a communications network such as the internet. Related methods for collecting particulate from a gas are also described in the referenced patent application.

There is a need to further ensure the integrity of collected particulate samples.

SUMMARY OF THE INVENTION

The present invention provides, in a first aspect, a sampling cartridge for a gas sampling apparatus. The cartridge includes a shell having a cylindrical wall and a sampling window extending through the wall. A spool is positioned adjacent the shell and has a sample collector located at a first circumferential location and a window closing surface located at a second different circumferential location. The spool and shell are rotatable relative to each other such that the sample collector and window closing surface can be selectively alternatively positioned adjacent the window for sample collection and cartridge sealing respectively. The self-sealing feature protects the collected particulate sample during cartridge removal, handling and transport.

The spool is preferably coaxial with and internal to the shell. The shell may be at least partially transparent to permit visual confirmation of previous use.

The spool may have a plurality of sample collectors at circumferentially spaced locations to permit sampling at different time intervals. Each of the sample collectors may comprise a foam or porous cloth material. The sample collector may preferably comprise a perforated foam material.

The cartridge may further include a fully encapsulated segment of the sample collector material as a negative control. The cartridge may also include memory means for storing chain of custody information about the cartridge. The chain of custody information can include personal identification information of a cartridge replenisher. Preferably, the memory means comprises a radio frequency tag which is serialized for traceability and write-protected to ensure single use of the cartridge.

The cartridge can further include a duration sample collector exposed through the window and separate from the spool. The duration sample collector may be mounted at a first circumferential location on a second spool which is independently rotatable relative to said shell. The second spool may include a second window closing surface at a second circumferential position. The first and second window closing surfaces may be automatically positioned adjacent the window whenever the cartridge is removed from the gas sampling apparatus.

The sampling cartridge may be combined with gas sampling apparatus having an access door. Preferably the cartridge is automatically sealed by positioning the window closing surface(s) adjacent the window, whenever the access door is opened. The gas sampling apparatus may further include a mandrel for mounting the cartridge and producing relative rotation between the shell and the spool(s).

The present invention provides, in a second aspect, a sampling cartridge for gas sampling apparatus which includes a cylindrical shell having a sampling window, and a pair of internal self-sealing sample substrate spools. Preferably, the shell is transparent and includes a radio frequency tag for storing chain of custody information relating to the cartridge. The chain of custody information may include personal identification information of a cartridge replenisher.

The cartridge may further include a fully encapsulated portion of virgin sample collector substrate material. The first spool may include multiple circumferentially spaced interval sample substrates while the second spool may include a single duration sample substrate. Each spool may further include a window closing surface. The first and second spools are independently rotatable relative to the shell, and each spool is self-sealed by rotating its window closing surface into alignment with the window.

The present invention provides, in a third aspect, a method of collecting a particulate sample with gas sampling apparatus having an access door. The method includes collecting the sample on a substrate, automatically sealing the substrate whenever the access door is opened, and recording chain of custody information on memory means associated with the substrate. The collection step may comprise collecting the sample on a substrate of a sampling cartridge. The sealing step may comprise self-sealing the cartridge. The recording step may comprise recording the chain of custody information for the cartridge on a radio frequency tag integral with the cartridge. The chain of custody information may include personal identification information of a cartridge replenisher. Further, the cartridge may incorporate a fully encapsulated portion of virgin substrate material as a negative control.

The present invention assures the integrity of collected particulate samples by employing a self-sealing sampling cartridge, automating the sealing of the cartridge upon opening of the access door of the gas sampling apparatus, incorporating a fully encapsulated portion of the virgin substrate material as a negative control, and storing chain of custody information on a Radio Frequency (RF) tag integral with the cartridge. These and other features, advantages and objects of the present invention will be more fully understood from the following detailed description of preferred embodiments.

BRIEF DESCRIPTION OF THE DRAWINGS

The subject matter which is regarded as the invention is particularly pointed out and distinctly claimed in the concluding portion of the specification. The invention, however, may best be understood by reference to the following, detailed description of various embodiments and the accompanying drawings in which:

DETAILED DESCRIPTION OF THE INVENTION

According to the principles of the present invention, gas sampling apparatus, such as the device described in commonly owned U.S. patent application Ser. No. 10/177,749, is provided with a self-sealing sampling cartridge. The cartridge is used to collect particulate or other material from sampled gas and is automatically sealed whenever the access door of the gas sampling apparatus is opened. The cartridge may include multiple interval sample collectors as well as a duration sample collector. Advantageously, the cartridge also includes a fully encapsulated segment of sample collector material to serve as a negative control, and memory means, e.g. a radio frequency (RF) tag, for storing chain of custody information, preferably including personal identification information of a cartridge replenisher. An outer shell of the cartridge may be at least partially transparent to permit visual confirmation of previous use of the cartridge. These features individually and collectively assure the integrity of collected particulate samples.

Figure 1:
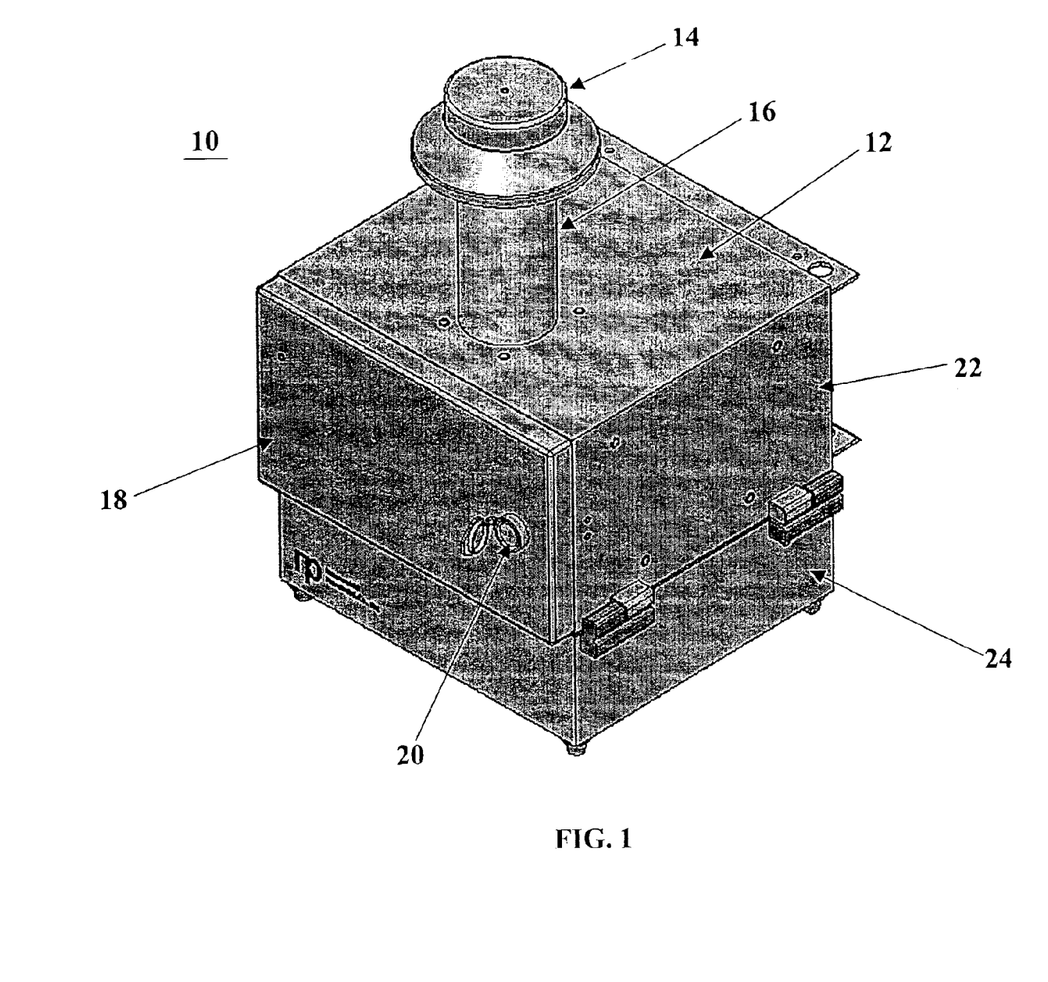
FIG. 1 is a front perspective view of the exterior of gas sampling apparatus in accordance with the present invention.

FIG. 1 presents an exterior view of gas sampling apparatus (10) which may employ the sampling cartridge of the present invention. Apparatus (10) generally includes a housing (12) having an inlet (14) connected by sample tube (16) to a top of housing (12), and an outlet (not shown). Inlet (14) may be any known inlet which serves to remove relatively large-sized particles from the gas and directs the sampled gas through tube (16) to a sample collector mounted on a sampling cartridge within housing (12). For example, inlet (14) may remove particles with a diameter of 10 micrometers or more from the sample gas.

Access door (18) may be hingedly mounted at the front of housing (12) to provide ready access to the components within housing (12). Access door (18) is preferably provided with a pick-proof lock (20).

Housing (12) may be conveniently divided into an upper section (22) containing the sampling components, and a lower section (24) containing electronics and communications equipment. The latter equipment can be used to control the operation of the sampling components and to provide external communication capabilities.

Figure 2:
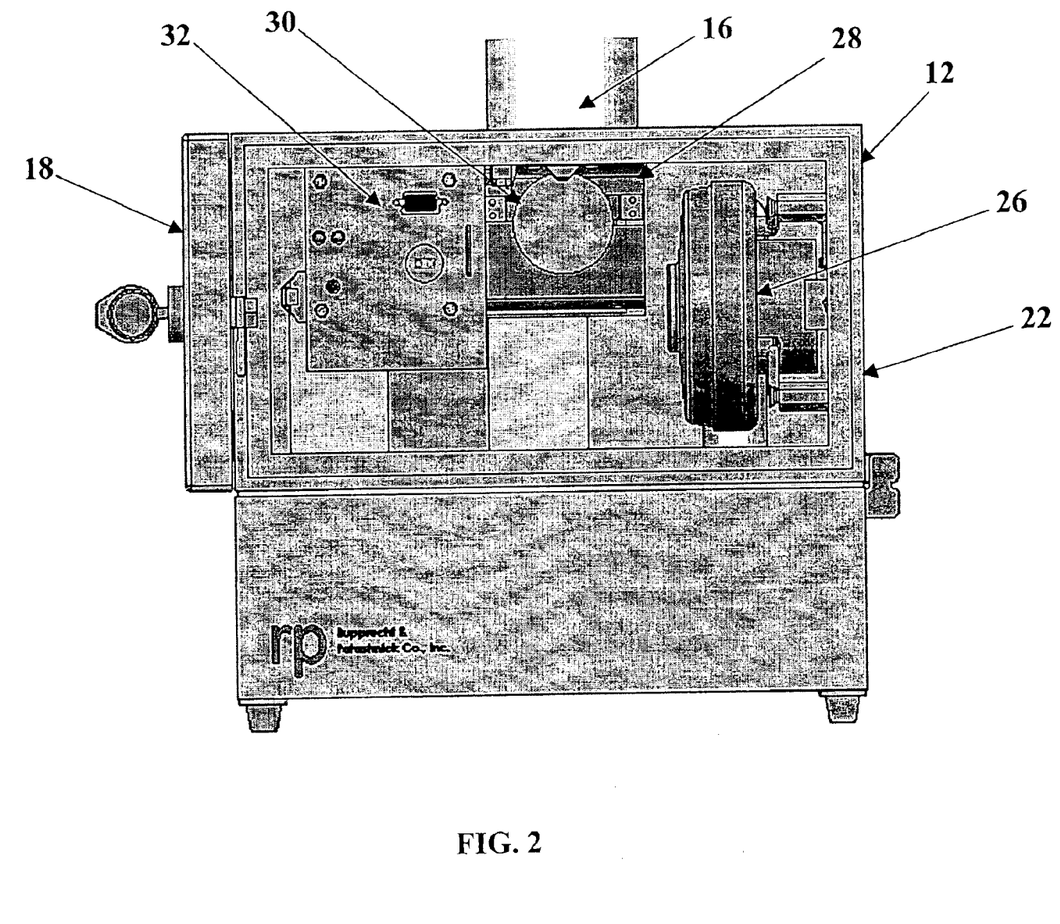
FIG. 2 is a front elevational view of the gas sampling apparatus with an access door opened.

FIG. 2 illustrates the components within the upper section (22) of housing (12) with the access door (18) opened. Located within section (22) is a blower or fan (26), sample collection equipment (28) including sampling cartridge (30), and a status panel (32).

High performance blower or fan (26) serves to draw gas through inlet (14), sample tube (16) and sampling equipment (28) so that samples of particulate matter may be collected. The fan produces a flow of gas of greater than about 50 liters per minute, and preferably greater than 200 liters per minute reducing the time to obtain a particulate sample for analysis. Fan (26) generates little noise so that a noise level emitted from the housing is less than about 60 decibels. To reduce the level of noise from apparatus (10) further, sound reducing material or insulation may be disposed on an inner surface of the housing. In addition, a muffler (not shown) may be disposed aft of the fan to further reduce the level of noise emitted by apparatus (10). A suitable high-flow rate, low-noise fan is manufactured and available from Ametek-Rotron of Saugerties, N.Y., Model No. MF 501. The use of such a fan also results in low power consumption. The gas sampling apparatus (10) may be connected to an AC power supply, or powered by a battery, and/or may include a back-up battery power supply.

Figure 3:
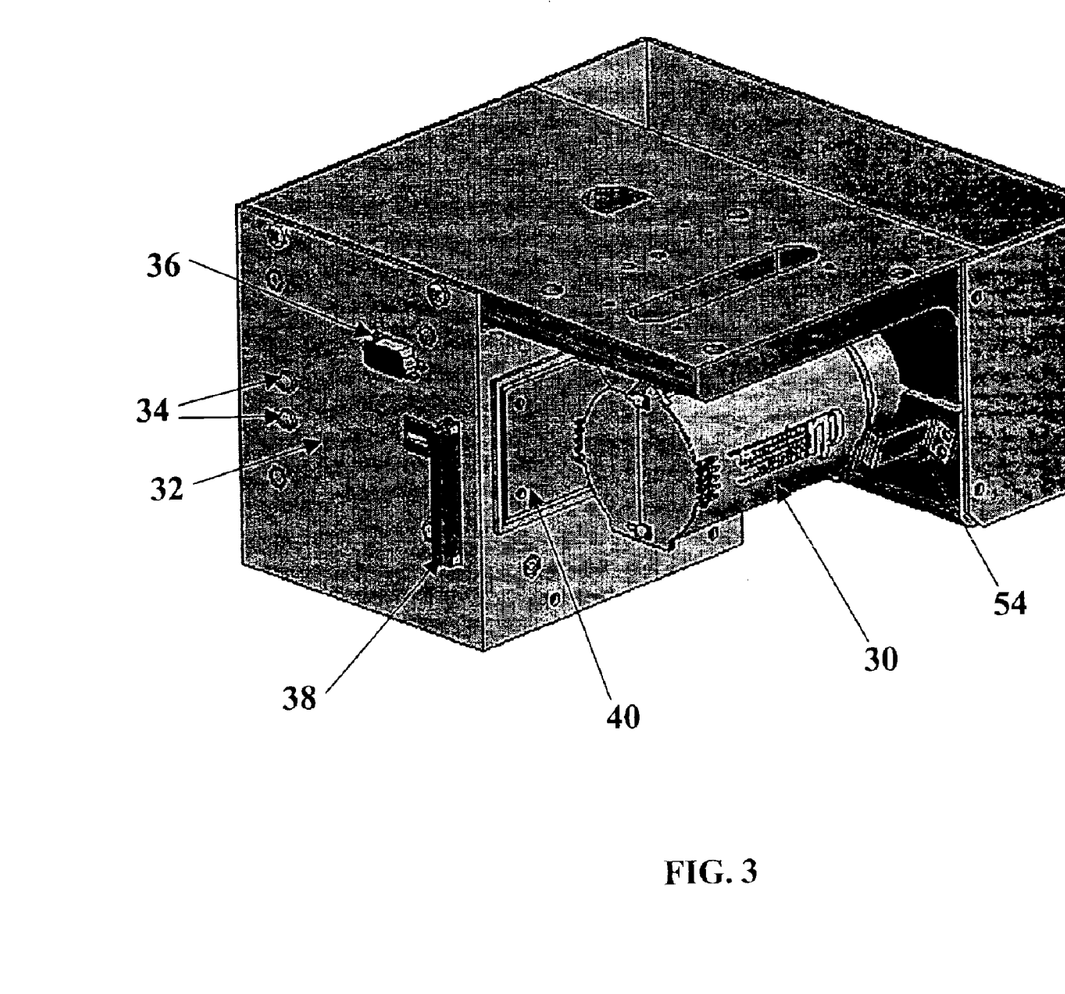
FIG. 3 is an enlarged perspective view of components of the gas sampling apparatus, including a sampling cartridge in accordance with the present invention.

As most clearly seen in FIG. 3, status panel (32) may include system status lights (34), communication ports, e.g. a RS-232 computer port (36) and a removable compact flash memory card (38). Compact flash memory card (38) is readily available in sizes from 32 to 256 MB and provides ample capacity to store second-by-second sensor data and other operating information of the gas sampling apparatus. The flash memory card also facilitates easy transfer of data to personal computers or through a network to a central monitoring station.

Mounted near status panel (32) is a radio frequency antenna (40) which, as is more fully described hereinafter, facilitates communication with an RF tag associated with sampling cartridge (30). The RF antenna (40) may transfer information to the RF tag, including chain of custody information for the sampling cartridge. Gas sampling apparatus (10) may advantageously be provided with the capability to read/validate personal identification information from a unique RF tag worn by a cartridge replenisher. The validation may occur through comparison to internally stored ID information or confirmation from a central monitoring station through a communications link. This replenisher identification information can be transmitted by the radio frequency antenna (40) for storage on a RF tag associated with a cartridge (30). The gas sampling apparatus may also broadcast the time and replenisher information from the cartridge to a central station. Replenisher ID information may be automatically stored on retrieved or newly installed cartridges, thus providing a tamper-evident system.

Figure 4:
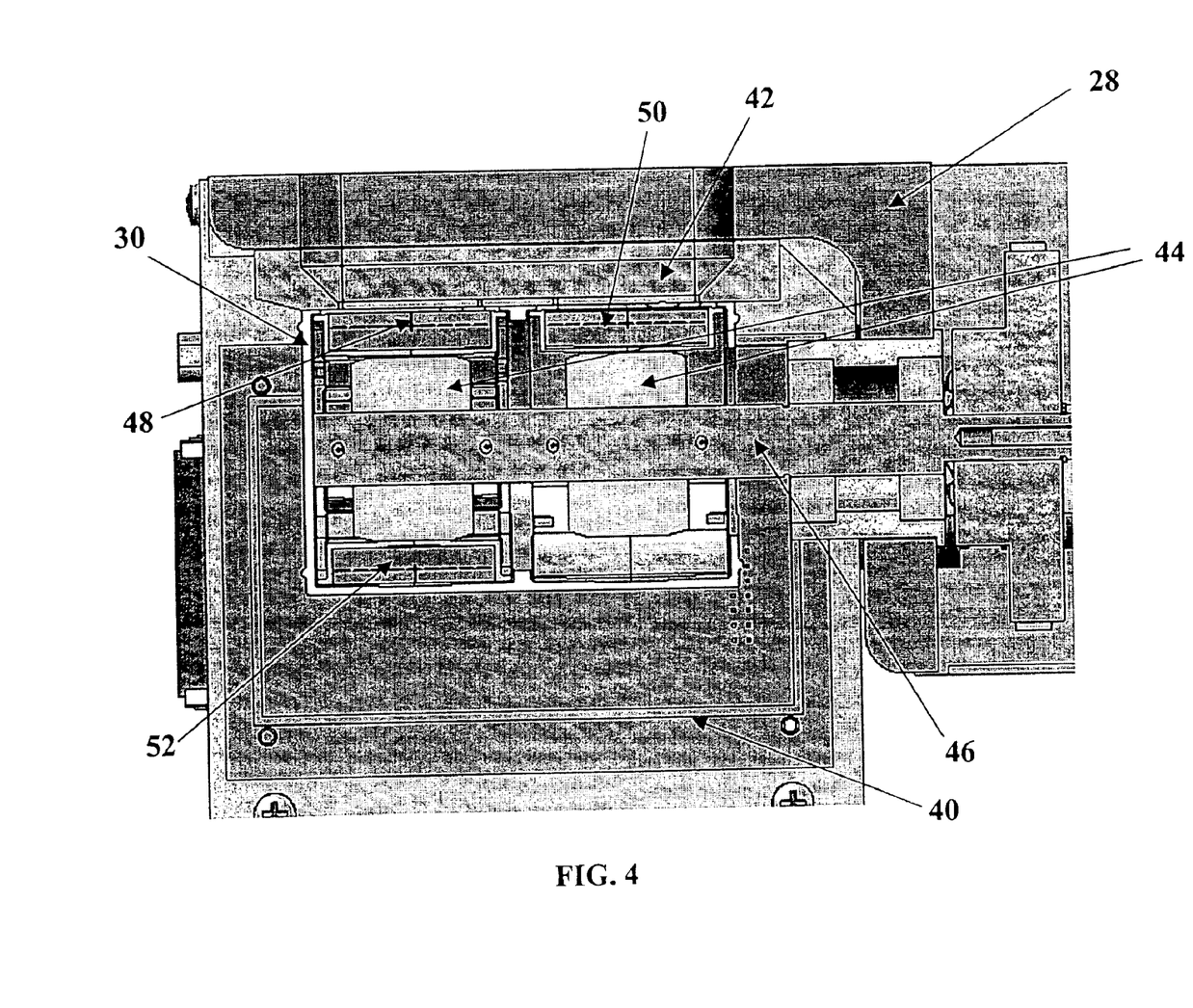
FIG. 4 is a longitudinal cross-sectional view through the mounted sampling cartridge of FIG. 3.

The particulate sampling equipment (28) includes an acceleration nozzle or slit(s) (42) sandwiched between sample tube 16 and sampling cartridge (30). As illustrated in FIG. 4, sampling cartridge (30) is mounted on a split mandrel (44) and inner shaft (46) in a position such that interval sample collectors (48) and a duration sample collector (50) on the cartridge are exposed to the sampled gas stream through slit(s) (42). Each sample collector is composed of a substrate (52) which serves to collect particulate from sampled gas that is channeled through nozzle or slit(s) 42 and impacts upon the collectors. Substrate (52) may be comprised of a foam or porous cloth material. Exemplary substrate materials include polyurethane, polyethylene, polypropylene, polyester or other suitable material. The substrate may be a porous material about 0.2 millimeters thick or greater. In one embodiment, the substrate may comprise a polyurethane foam material having a density of about $0.005$ g/cm$^3$ to about $0.1$ g/cm$^3$. Particulate with a size of about 1.0 micron and larger may be collected on such a substrate.

Advantages of the impact collector comprising a foam or porous cloth material include permitting a high-flow rate of air to be sampled without clogging the collector or the slit, reducing particle bounce, eliminating the need to oil the substrate, inhibiting an increase in the pressure drop on the substrate as particles are accumulated on the substrate, concentrating the collection of particles in the upper portion of the substrate, and allowing the substrate to be formed from a generally inert material. While a slit impactor is shown, it will be appreciated that other shaped openings may be employed. Further, impact collectors for use in the apparatus of the present invention are disclosed in U.S. Pat. No. 6,435,043, entitled "Impaction Substrate and Methods of Use" issued on Aug. 20, 2002.

A radioactivity sensor (not shown) may be employed to detect and signal, in real time, the presence of radioactive material in the gas and/or collected particulate, as described in U.S. patent application Ser. No. 10/177,794.

Figure 5:
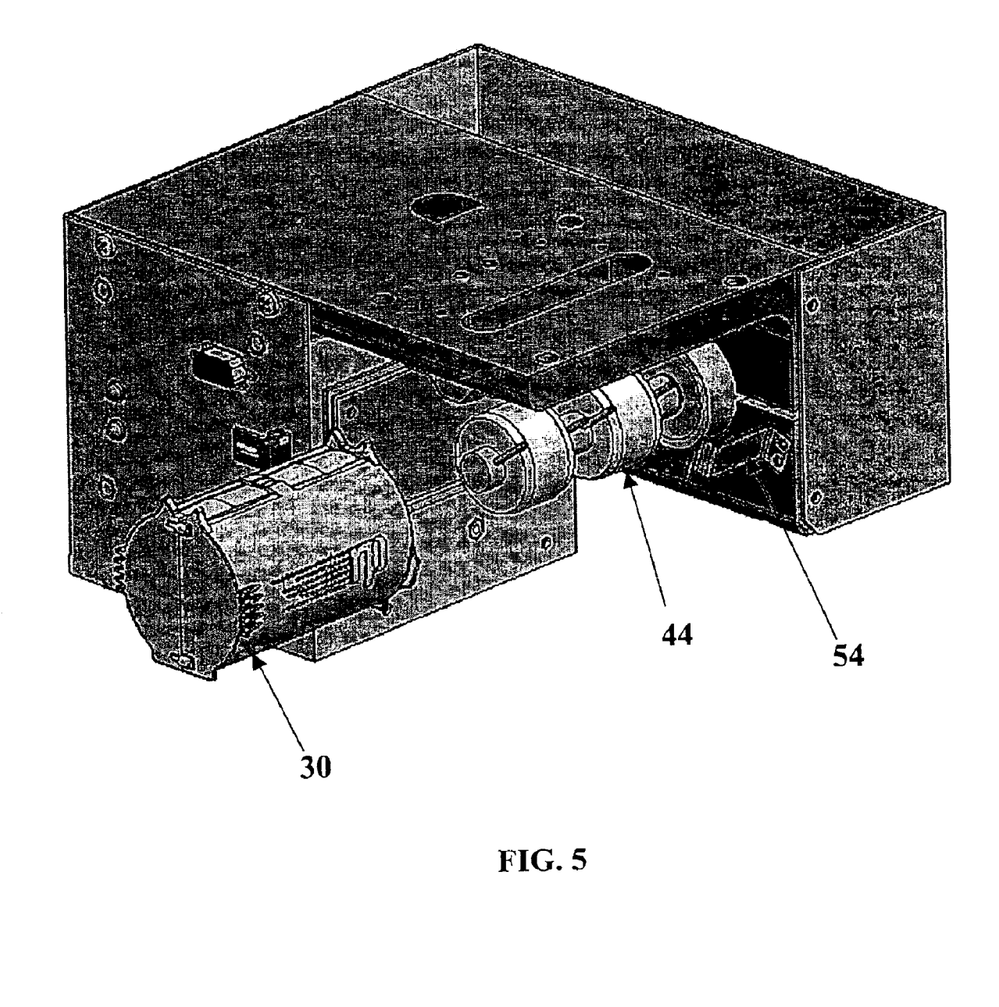
FIG. 5 is a perspective view showing the sampling cartridge removed from the supporting mandrel.

Cartridge (30) is retained on mandrel (44) by spring catches (54) (FIG. 3). As shown in FIG. 5, these catches disengage themselves when the cartridge is removed from the mandrel.

When cartridge (30) is removed, a sampling window (56) of the cartridge is always sealed with a window closing surface 58, as more fully described hereinafter. The gas sampling apparatus (10) is configured such that whenever its access door (18) is opened, installed cartridge (30) is automatically sealed. The sealing operation is described below.

Figure 6:
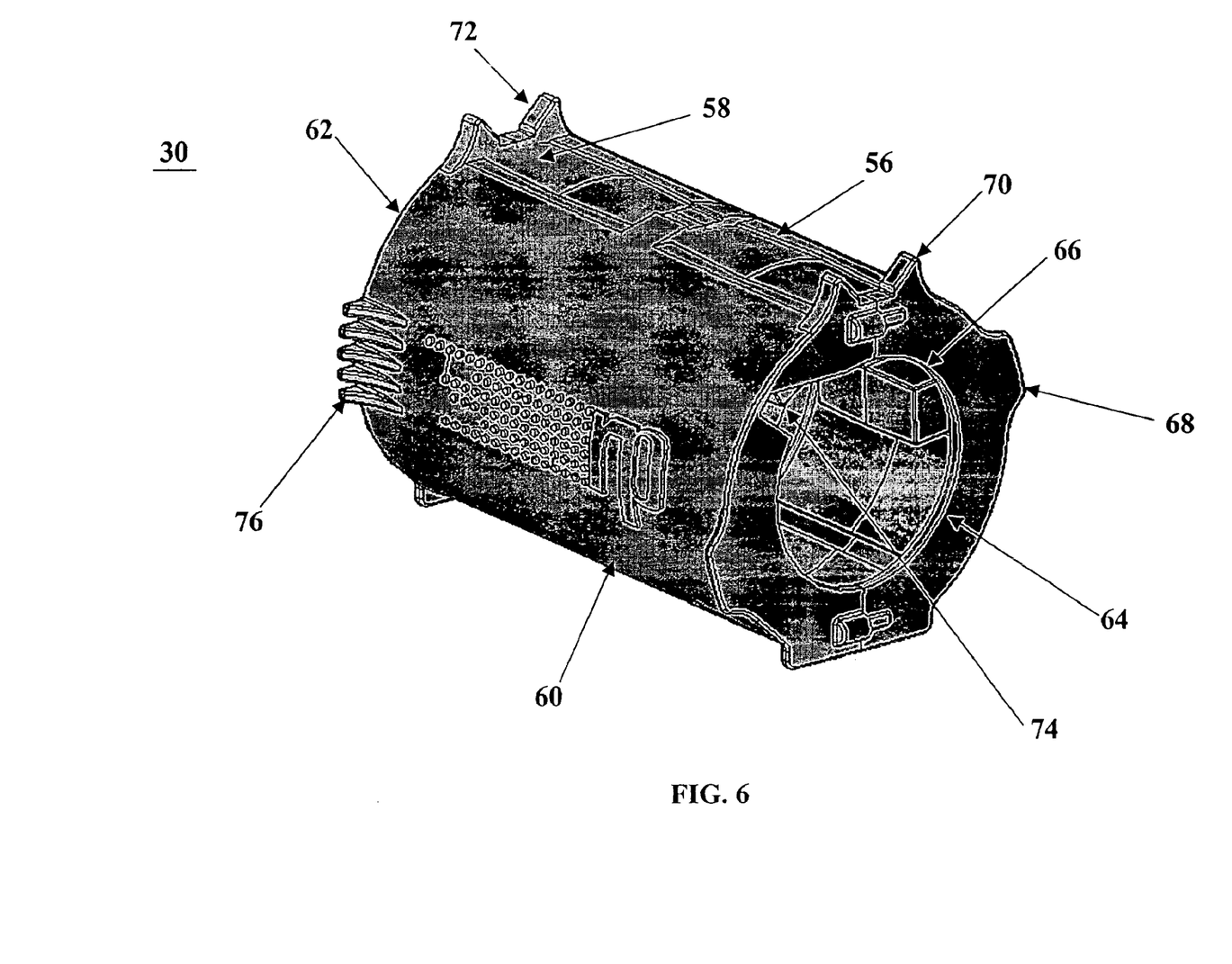
FIG. 6 is a perspective view from the mounting end of the sealed sampling cartridge of the present invention.

FIG. 6 illustrates sampling cartridge (30) with its window (56) sealed by window closing surface (58). Cartridge (30) is preferably always sealed during handling and transport by a cartridge replenisher. Gas sampling apparatus (10) opens the cartridge after the cartridge is mounted in the housing and the access door is locked. The gas sampling apparatus re-seals the cartridge whenever the door is unlocked and opened.

Referring still to FIG. 6, sampling cartridge (30) has a cylindrical shell or casing (60) completely closed at one end by an end cap (62). At the other end of shell (60) is a slotted ring (64) with an opening (66) for receiving mandrel (44). Ring (64) includes a pair of tabs (68) which engage spring catches (54) to retain cartridge (30) on the mandrel. Ring (64) also incorporates a pair of ears (70) which together with another set of ears (72) at the other end of the cartridge engage nozzle (42). Ring (64) also has a slot (74) for spool engagement keys. Finger tabs (76) are provided at the outer end of cartridge (30) to facilitate removal of the cartridge for replenishment.

Figure 7:
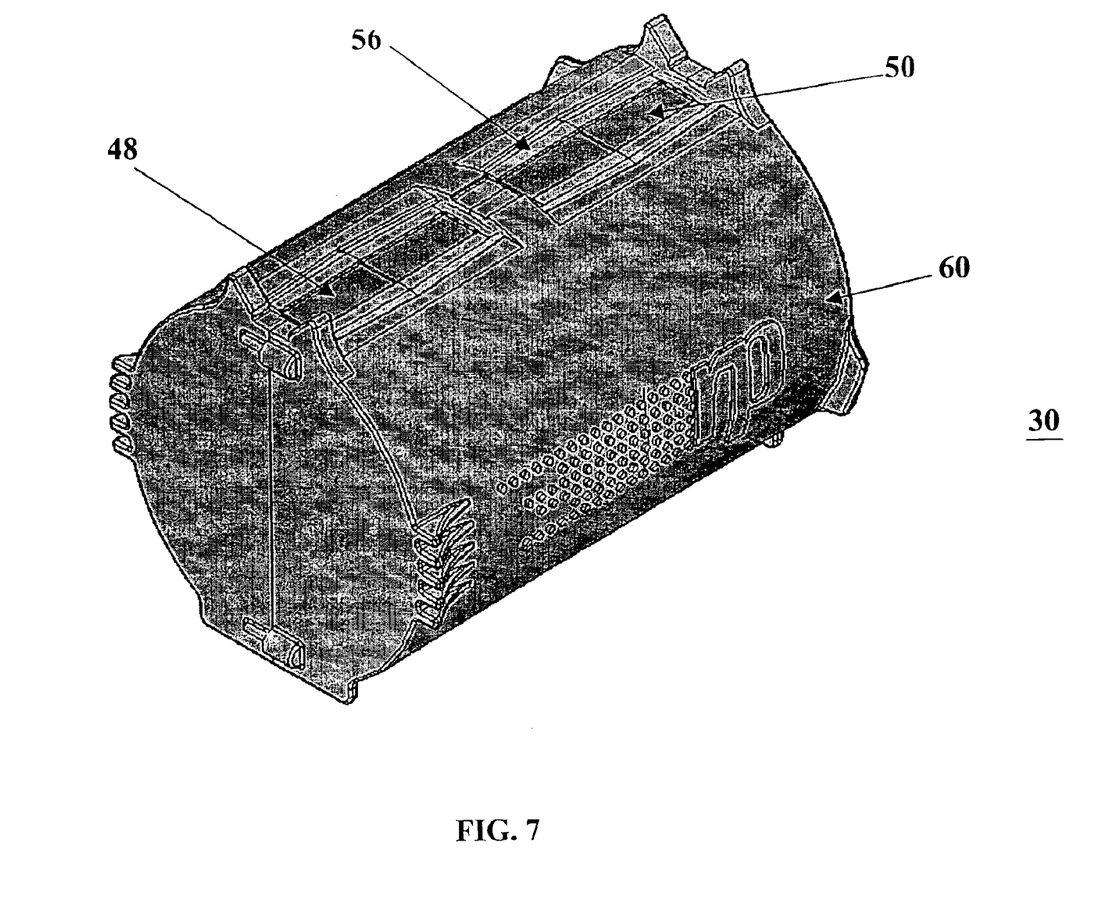
FIG. 7 is a perspective view of the sampling cartridge with exposed sample collectors.

FIG. 7 shows sampling cartridge (30) in its sampling or open state. In this state, interval sample collectors (48) and duration sample collector (50) are exposed to the sample gas stream through window (56). As illustrated, interval sample collectors (48) and duration sample collector (50) may be formed in pre-cut and/or pre-perforated segments.

Figure 8:
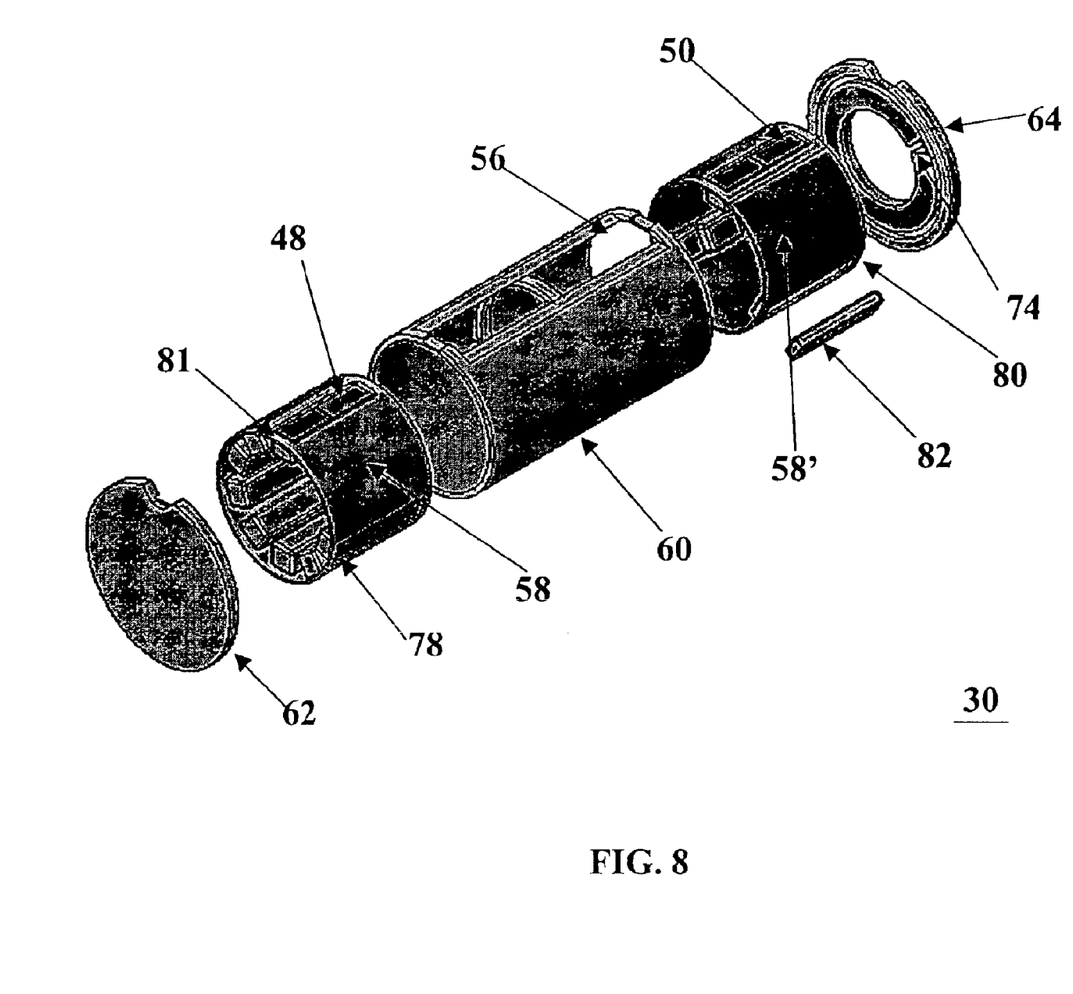
FIG. 8 is a simplified exploded view of a multi-interval sampling cartridge.

Referring now to FIG. 8, in a preferred embodiment, sampling cartridge 30 includes a pair of independently rotatable inner spools (78) and (80) coaxial with and internal to shell (60). First or interval spool (78) may include multiple sample collectors (48) circumferentially spaced around the spool for sampling the gas during different predetermined intervals (time resolved intervals). Spool (78) also includes a window closing surface (58) at a predetermined circumferential location. Spool (78) is rotated by mandrel (44) under control of suitable drive means to expose different sample collectors (48) during sampling, and is automatically rotated to place window closing surface (58) adjacent window (56) to seal the cartridge whenever the access door of the gas sampling apparatus is opened. The processor or controller (not shown) of the apparatus can detect opening of the access door through a suitable switch or sensor, and causes the mandrel drive means to seal the cartridge in response thereto.

The second or duration spool (80) includes a duration sample collector (50) which can be exposed to the sampling gas through window (56) of shell (60) throughout the sampling period (long duration sampling). Like spool (78), duration spool (80) includes a window closing surface (58') which may be automatically rotated to a position adjacent window (56) for sealing the cartridge whenever the access door of the gas sampling apparatus is opened. Since sample collectors (48) and (50) are contained in individual pockets (81) of the respective spools, when window closing surfaces (58) and (58') are positioned adjacent window (56), the sample collectors and any collected particulate are completed sealed off. Cartridge (60) is thus self-sealing. Duration spool (80) may also be provided with a pocket for receiving a fully encapsulated segment (82) of sample collector material which may serve as a negative control.

Figure 9:
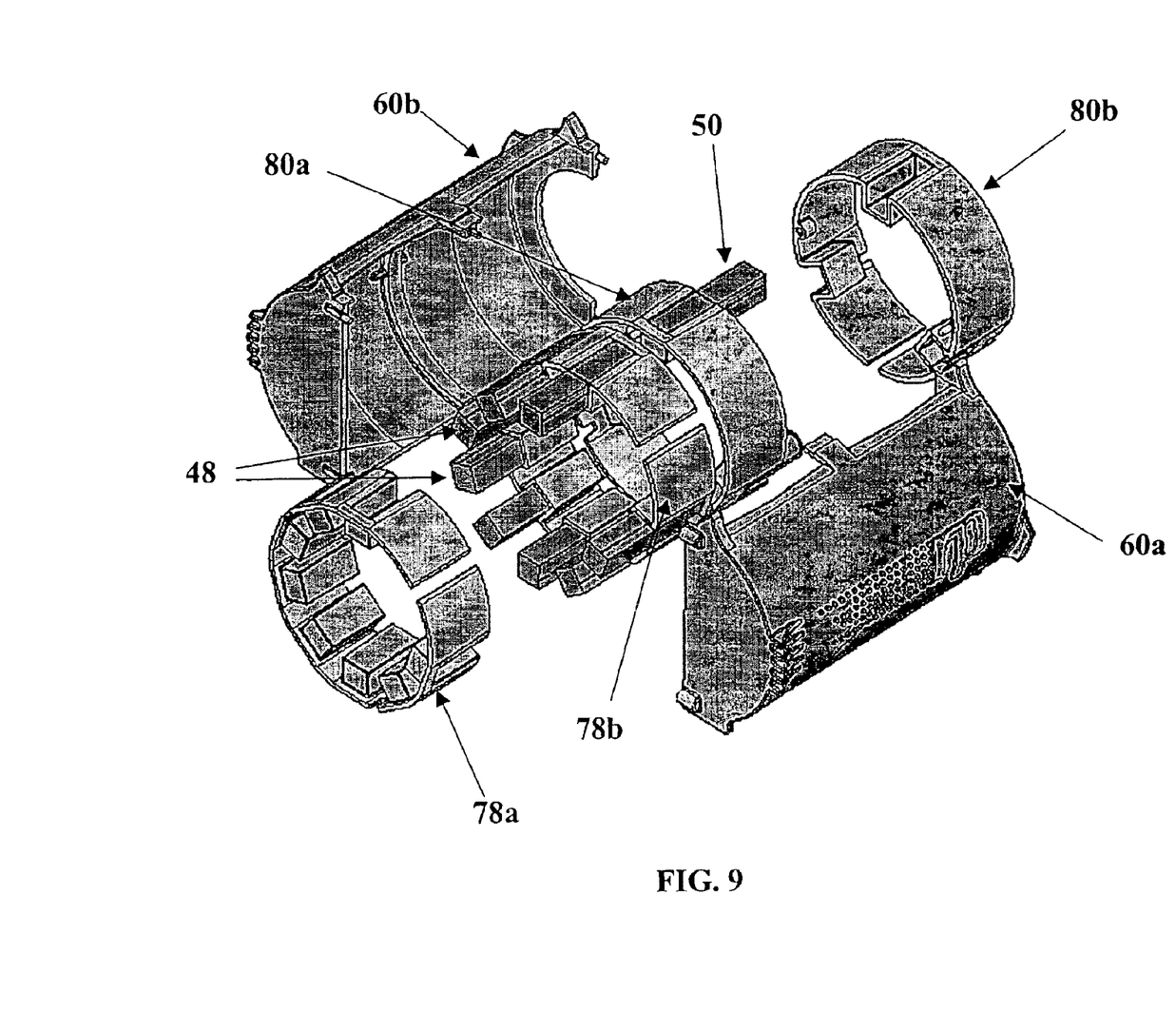
FIG. 9 is a more detailed exploded view of an embodiment of a multiple interval sampling cartridge.

In one practical implementation, as shown in FIG. 9, the outer shell may be formed in two parts (60a), (60b) and each of the independently rotatable spools may be formed in two parts (78a), (78b) and (80a), (80b), respectively. Interval spool (78) may contain eight circumferentially spaced interval sample collectors (48) while duration spool (80) contains a single duration sample collector (50). Each sample collector may be pre-perforated in a longitudinal direction into multiple, e.g. four parts and also pre-perforated at a desired depth, e.g. 0.090 inches. Such pre-perforation allows for optimal sample extraction for subsequent analysis.

The outer shell and internal spools, as well as the end plate and end ring may be manufactured in a variety of different known ways, for example, molded, and may be made of any suitable material, e.g. plastic. The cartridge may have a size approximately 2 inch diameter by 2.75 inches long, or other sizes. Outer shell (60) is preferably at least partially transparent to permit visual confirmation of previous use of the cartridge.

The number, shape, type and location of the sample collectors in spools (78) and (80) may vary from that shown in the illustrative embodiment. For example, interval spool (78) may for certain applications include just a single interval sample collector (48).

Figure 10:
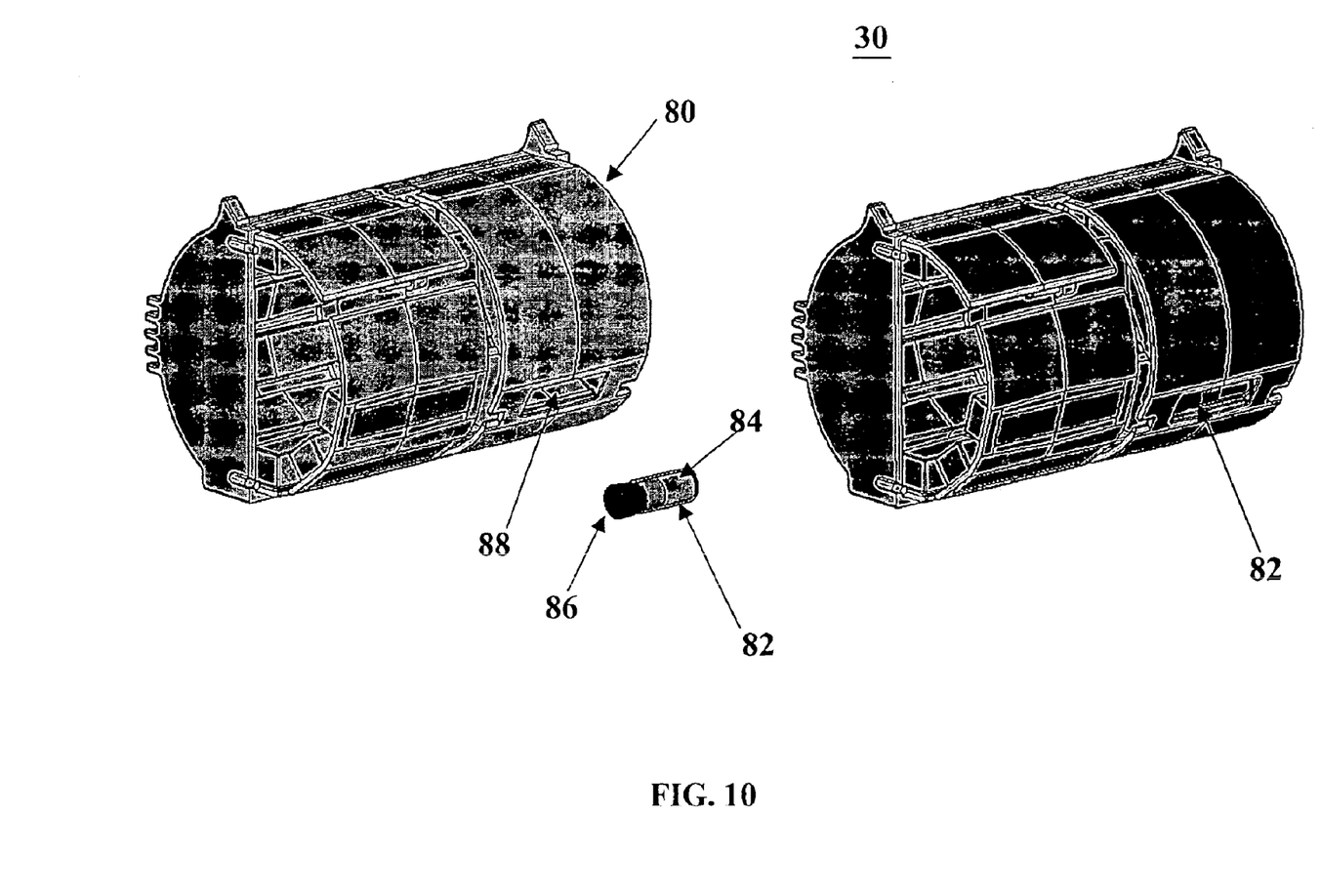
FIG. 10 is a partially cut-away perspective view showing the placement of an encapsulated segment of sample collector material in the sampling cartridge for use as a negative control.

The incorporation of a fully encapsulated segment of substrate material as a negative control in the sampling cartridge (30) is illustrated in FIG. 10. As shown, a portion or segment (82) of virgin sampling substrate (52) used to form sample collectors (48) and (50), is placed in a vial (84) and sealed therein with a cap (86). Vial (84) may then be placed in a dedicated pocket (88) formed in duration spool (80). For clarity of illustration, cartridge (30) is shown in FIG. 10 with the half (60a) of shell (60) removed. The fully encapsulated substrate material (82) may be used to verify substrate material purity, e.g. if a biohazard test of collected particulate is positive. Vial (84) may be removed from cartridge (30) by rotating duration spool (80) so that pocket (88) is aligned with window (56). Vial (84) can then be removed through the sampling window without opening cartridge (30).

Figure 11:
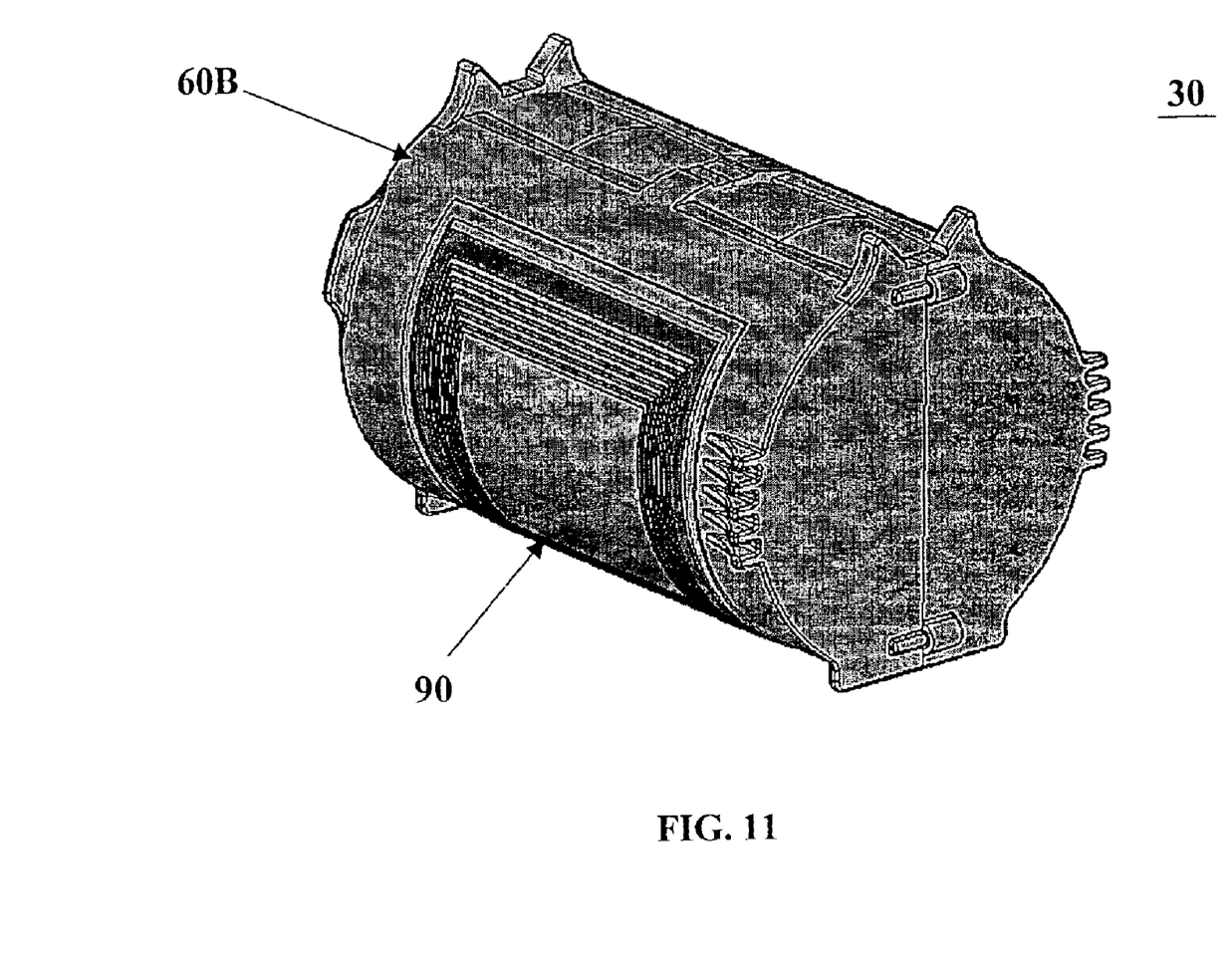
FIG. 11 is a perspective view of a sampling cartridge with an integral radio frequency tag.

Data storage or memory means may be associated with the sampling cartridge. As shown in FIG. 11, a radio frequency (RF) tag (90) may be integrally formed with the left part (60b) of the shell (60) of sampling cartridge (30). Such RF tags are known and have in the past been used for product identification purposes. In the present invention, an RF tag (90) integral with the cartridge (30) is not only serialized for unique traceability but is also used to store chain of custody information for the associated cartridge. As earlier described, such chain of custody information may include personal identification information of a cartridge replenisher. Preferably, data recorded on the RF tag is write-protected to ensure single use of the sampling cartridge. Once sampling is complete, sampling cartridge (30) is removed from gas sampling apparatus (10) in sealed state, and may be placed in sealed plastic bags for transport to an analysis station. The RF tags permit individual or multiple sampling cartridges to be read through the transport bags. The RF tags also provide for automatic data recording and reading.

The integrity of the collected samples and the sampling process is assured, by the present invention, through the provision of the self-sealing sampling cartridge, the automatic sealing of the cartridge whenever the access door of the gas sampling apparatus is opened and the incorporation of the negative control material within the cartridge. The use of two independently rotatable spools within the cartridge allows sampling flexibility. The integral RF tag facilitates storage of chain of custody information including personal identification information relating to the cartridge replenisher. These and the other unique features of the present invention provide for a significantly improved gas sampling apparatus and method which are uniquely suited for wide application and secure operation.

While various embodiments of the present invention have been illustrated and described, it will be appreciated by those skilled in the art that many modifications and changes may be made thereunto without departing from the spirit and scope of the invention.

What is claimed is:

1. A method of collecting a particulate sample with gas sampling apparatus having an access door, comprising:
   collecting the sample on a substrate;
   automatically sealing the substrate whenever the access door is opened; and
   recording chain of custody information on memory means associated with the substrate.

2. The method of claim 1, wherein the substrate comprises a substrate of a sampling cartridge, said sealing comprises self-sealing said cartridge, and said recording comprises recording the chain of custody information on a radio frequency tag integral with the cartridge.

3. The method of claim 2, wherein said chain of custody information includes personal identification information of a cartridge replenisher.

4. The method of claim 2, further including incorporating a fully encapsulated portion of virgin substrate material as a negative control in said cartridge.

* * * * *